United States Patent
Doria et al.

[11] Patent Number: 5,206,258
[45] Date of Patent: Apr. 27, 1993

[54] USE OF HETEROARYL-3-OXO-PROPANENITRILE DERIVATIVES IN TREATING CLINICAL WHEREIN MYELOPOIESIS SUPPRESSION OCCURS

[75] Inventors: Gianfederico Doria, Milan; Anna M. Isetta, Rho; Rinaldo Ferreccio, Gorgonzola; Mario Ferrari, Milan; Maria C. Fornasiero, Vigevano; Domenico Trizio, Cassina Rizzardi, all of Italy

[73] Assignee: Farmitalia Carlo Erba S.r.l., Milan, Italy

[21] Appl. No.: 663,843

[22] PCT Filed: Jul. 11, 1990

[86] PCT No.: PCT/EP90/01129
§ 371 Date: Mar. 12, 1991
§ 102(e) Date: Mar. 12, 1991

[87] PCT Pub. No.: WO91/01309
PCT Pub. Date: Feb. 7, 1991

[30] Foreign Application Priority Data
Jul. 17, 1989 [GB] United Kingdom ............ 8916290.3

[51] Int. Cl.$^5$ .............. A61K 31/415; C07D 231/54; C07D 49/052; C07D 495/04
[52] U.S. Cl. ............................. 514/403; 514/333; 514/338; 514/407; 546/256; 546/271; 546/279; 548/359.1; 548/359.5
[58] Field of Search ............ 548/359; 514/403

[56] References Cited
U.S. PATENT DOCUMENTS

| | | | |
|---|---|---|---|
| 3,404,157 | 10/1968 | McEvoy et al. | 548/359 |
| 3,969,527 | 7/1976 | Krapcho et al. | 514/403 |
| 4,140,755 | 2/1979 | Hoffman et al. | 548/359 X |
| 4,409,234 | 10/1983 | Fujimura et al. | 514/403 |
| 4,420,476 | 12/1983 | Philipp et al. | 548/359 X |
| 4,816,467 | 3/1989 | Doria et al. | 514/333 |

FOREIGN PATENT DOCUMENTS

| | | | |
|---|---|---|---|
| 0274443 | 7/1988 | European Pat. Off. | 514/403 |
| 60-130521 | 7/1985 | Japan | 514/403 |
| 62-99361 | 5/1987 | Japan | 514/403 |
| WO89/12630 | 12/1989 | World Int. Prop. O. | 514/403 |
| WO89/12638 | 12/1989 | World Int. Prop. O. | 514/403 |

Primary Examiner—Floyd D. Higel
Attorney, Agent, or Firm—Nikaido Marmelstein Murray & Oram

[57] ABSTRACT

Heteroaryl-3-oxo-propanenitrile derivatives of formula (I)

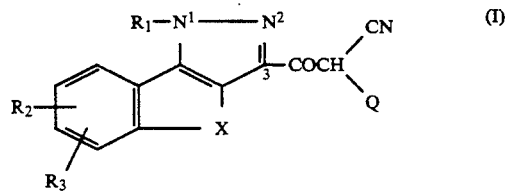

wherein
X represents an oxygen atom or a $-CH(R_4)-$, $-O-CH(R_4)-$, $-S(O)_n-$, $-S(O)_n-CH(R_4)-$, $-CH(R_4)-O-$, $-CH(R_4)-S(O)_n-$ or $-CH(R_4)-CH_2-$ group wherein n is 0, 1 or 2; $R_1$ represents $C_1-C_6$ alkyl, pyridyl or unsubstituted or substituted phenyl; $R_2$, $R_3$ and $R_4$ are as herein defined; and Q is hydrogen, carboxy, $C_2-C_7-$ alkoxycarbonyl or a $-CON(R_a)R_b$ group, $R_a$ and $R_b$ being as defined herein; and their pharmaceutically acceptable salts are useful in stimulating myelopoiesis in bone marrow suppressed mammals.

4 Claims, No Drawings

USE OF HETEROARYL-3-OXO-PROPANENITRILE DERIVATIVES IN TREATING CLINICAL WHEREIN MYELOPOIESIS SUPPRESSION OCCURS

Suppression of myelopoiesis is a frequent and sometimes life-threatening side-effect of the chemo- and radio-therapy in cancer and of the drugs used to treat rheumatoid arthritis and other autoimmune diseases.

Suppression of myelopoiesis is common also in patients with severe burns and bone marrow disorders and in subjects that undergo organ transplantation, who are given immuosuppressant drugs to minimize the danger of rejection.

To find a drug which is effective in stimulating myelopoiesis in bone marrow suppressed patients still remains an important target for the today's Medicinal Chemistry, with large potential clinical application.

The present invention relates, in one aspect, to a method of stimulating myelopoiesis in bone marrow suppressed mammals, including humans, which comprises administering to said mammals, in need of such treatment, a therapeutically effective amount of an active heteroaryl-3-oxo-propanenitrile derivative of formula (I), as herein defined, or a pharmaceutically acceptable salt thereof.

In another aspect this invention relates to the use of a heteroaryl-3-oxo-propanenitrile derivative of formula (I), as herein defined, or a pharmaceutically acceptable salt thereof in the preparation of a pharmaceutical composition for the use in stimulating myelopoiesis in bone marrow suppressed mammals, including humans.

Examples of pathological ocnditions in which a suppressed myelopoiesis takes place, which can be treated by the compounds of formula (I) or by the pharmaceutical compositions containing them, according to the method of treatment of the present invention, are those which occur in the case of cancer chemotherapy and cancer radiation therapy; in immunosuppressant therapy used for organ or tissue transplantation; in immunosuppressant therapy in the case of an autoimmune disease; in the case of autologous and allogenic bone marrow transplants; in the case of severe burns; in the case of accidental exposure to radiation or to certain chemicals, e.g. benzene, and in the case of aplastic anemia, myelodysplastic syndrome and congenital or acquired bone marrow disorders.

The heteroaryl-3-oxo-propanenitrile derivatives which are effective in stimulating myelopoiesis in bone marrow suppressed mammals and are useful in the method of treatment, or in the preparation of the pharmaceutical compositions, according to the present invneiton, are described in our patent applications EP-A-0274443, WO 89/12630, WO 89/12638 and British patent applicaton No. 8902596.9, and can be represented by the following formula (I)

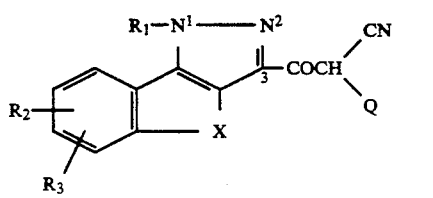

wherein
X represents
a) an oxygen atom or a $—S(O)_n—$ group, wherein n is zero, 1 or 2;
b) a $—CH(R_4)—$ group, wherein $R_4$ represents hydrogen or $C_1—C_6$ alkyl;
c) a

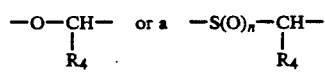

group, wherein n and $R_4$ are as defined above;
d) a

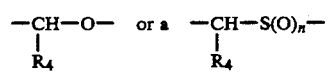

group, wherein n and $R_4$ are as defined above; or
e) a

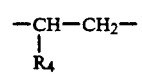

group, wherein $R_4$ is as defined above;

$R_1$ represents $C_1-C_6$ alkyl, pyridyl or phenyl, the phenyl being unsubstituted or substituted by one or two substituents chosen independently from halogen, trifluoromethyl, $C_1-C_6$ alkyl, $C_1-C_6$ alkoxy, nitro, amino, formylamino and $C_2-C_8$ alkanoylamino; $R_2$ represents:
a) hydrogen, halogen or $C_1-C_6$ alkyl;
b) hydroxy, $C_1-C_6$ alkoxy or $C_3$ or $C_4$ alkenyloxy;
c) nitro, amino, formylamino or $C_2-C_8$ alkanoylamino;
d) di ($C_1-C_6$ alkyl) amino or a

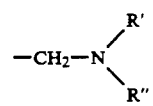

group
wherein each of R' and R" independently is $C_1-C_6$ alkyl or R' and R", taken together with the nitrogen atom to which they are linked, form a heterocyclic ring which is selected from N-pyrrolidinyl, N-piperazinyl, hexahydroazepin-1-yl, thiomorpholino, morpholino and piperidino and which is unsubstituted or substituted by $C_1-C_6$ alkyl:
e) $—CH_2OH$, $—CHO$, $—COOH$ or $C_2-C_7$ alkoxycarbonyl;
f) a

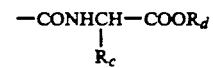

group
wherein $R_d$ is hydrogen or $C_1-C_6$ alkyl and $R_c$ is hydrogen, phenyl or the side-chain of an α-aminoacid;
g) a $$-\text{NHCOCH}-\text{NH}_2$$
$$\quad\quad\quad |$$
$$\quad\quad\quad R_c$$

group,
   wherein $R_c$ is as defined above;
   h) a $$-\text{CH}_2\text{P} \overset{\text{O}}{\underset{\text{OR}}{\diagdown}} ^{\text{OR}},$$

a
      $-\text{CH}_2\text{OCO}(\text{CH}_2)_n\text{COOR}$ or a $-\text{NHCO}(\text{CH}_2)_n\text{COOR}$ group, wherein n is as defined above and R is hydrogen or $C_1$-$C_6$ alkyl;
   k) a $-\text{CH}=\text{N}-\text{OR}'_1$ group wherein $R'_1$ is hydrogen or a $-\text{CH}_2\text{COOH}$ group;
   i) a $-\text{CH}=\text{N}-\text{NH}-R'_2$ group wherein $R'_2$ is hydrogen, $-\text{CH}_2\text{CH}_2\text{OH}$, $C_2$ or $C_3$ alkoxycarbonyl or a $-(\text{CH}_2)_p-R'_3$ group wherein p is 1 or 2 and $R'_3$ is COOH or $C_2$-$C_7$ alkoxycarbonyl;
   l) a $$-\text{CH}=\text{N}-\text{N}=\text{CH}-\text{N} \diagdown^{R'}_{R''}$$

group
   wherein R' and R" are as defined above; or
   m) a $$-\text{N}=\text{CH}-\text{N} \diagdown^{R'}_{R''}$$

group
   wherein R' and R" are as defined above;
   n) a $C_2$-$C_7$ alkoxycarbonyl group substituted by a $$-\text{N} \diagdown^{R'}_{R''}$$

group,
   wherein R' and R" are as defined above; $R_3$ is as $R_2$ defined above under a), b), and c); Q represents hydrogen, carboxy, $C_2$-$C_7$ alkoxycarbonyl or a $$-\text{CON} \diagdown^{R_a}_{R_b}$$

group
   wherein $R_a$ represents hydrogen or $C_1$-$C_{20}$ alkyl and $R_b$ represents $C_1$-$C_{20}$ alkyl, a $$-\text{CH}-\text{COOR}_d$$
$$\quad |$$
$$\quad R_c$$

group
   wherein $R_3$ and $R_c$ are as defined above or a $-(A)_m-R_5$ group wherein m is zero or 1, A is a $C_1$-$C_6$ alkylene chain and $R_5$ is
   a') $C_5$-$C_8$ cycloalkyl;
   b') pyridyl, unsubstituted or substituted by one or two substituents chosen independently from halogen, $C_1$-$C_6$ alkyl and $C_1$-$C_6$ alkoxy;
   c') phenyl, unsubstituted or substituted by one or two substituents independently chosen from halogen, $CF_3$, $C_1$-$C_6$ alkyl, $C_1$-$C_6$ alkoxy, amino, nitro, formylamino, $C_2$-$C_8$ alkanoylamino, di($C_1$-$C_6$ alkyl)-amino, hydroxy, formyloxy and $C_2$-$C_8$ alkanoyloxy;
   d') phenyl substituted by a $-\text{CH}_2\text{OH}$, COOH, $C_2$-$C_7$
   alkoxycarbonyl or a $$-\text{CH}_2-\text{N} \diagdown^{R'}_{R''}$$

group
   wherein R' and R" are as defined above and optionally by another substituent chosen from halogen, $C_1$-$C_6$ alkyl, $C_1$-$C_6$ alkoxy, amino, nitro, formylamino, $C_2$-$C_8$ alkanoylamino, hydroxy, formyloxy and $C_2$-$C_8$ alkanoyloxy, or
   e') 2-thienyl, 2-furyl or 1-($C_1$-$C_6$ alkyl)-pyrrol-2-yl; or
   f') a heterocyclic ring which is selected from 2-pyrimidyl, 2-thiazolyl and 3-isoxazolyl and which is unsubstituted or substituted by $C_1$-$C_6$ alkyl.

It has to be noticed that the compounds of formula (I) may be represented also by a tautomeric structure, namely the enol structure of formula (Ia)

$$\begin{array}{c} R_1-N \text{———} N \\ \diagup \quad\quad\quad \diagdown \\ R_2- \phantom{XX} \text{C}=\text{C} \diagup^{\text{CN}} \\ \phantom{XXXXX} | \quad\quad \diagdown_{\text{Q}} \\ R_3- \phantom{XX} X \quad \text{OH} \end{array} \quad (\text{Ia})$$

wherein
   X, $R_1$, $R_2$, $R_3$ and Q are as defined above. However, the compounds of formula (Ia), which fall within the scope of the present invention too, are described in the present specification as compounds of formula (I).

A halogen atom is preferably chlorine or fluorine.

The alkyl, alkylene, alkanoyloxy, alkoxy and alkanoylamino groups may be branched or straight chain groups.

A $C_1$-$C_{20}$ alkyl group is preferably a $C_1$-$C_{10}$ alkyl group, or example a $C_1$-$C_6$ alkyl grup. A $C_1$-$C_6$ alkyl group is, e.g., methyl, ethyl, propyl, isopropyl, butyl or tert.butyl. A $C_1$-$C_4$ alkyl group is more preferred such as methyl, ethyl or tert.butyl.

A $C_3$ or $C_4$ alkenyloxy group is preferably allyloxy.

A $C_1$-$C_6$ alkoxy group is, e.g., methoxy, ethoxy, propoxy, isopropoxy, butoxy or tert.butoxy. Preferably it is a $C_1$-$C_4$ alkoxy group such as methoxy, ethoxy or propoxy.

A $C_5$-$C_8$ cycloalkyl group is preferably cyclopentyl or cyclohexyl.

A C$_2$–C$_8$ alkanoylamino group is preferably a C$_2$–C$_6$ alkanoylamino group, for example a C$_2$–C$_4$ alkanoylamino group such as acetylamino or propionylamino. A C$_2$–C$_8$ alkanoyloxy group is preferably a C$_2$–C$_6$ alkanoyloxy group, for example a C$_2$–C$_4$ alkanoyloxy group such as acetoxy or propionyloxy.

A C$_2$–C$_7$ alkoxycarbonyl group is preferably a C$_4$–C$_7$ alkoxycarbonyl group, in particular a tertiary C$_4$–C$_7$ alkoxycarbonyl group such as tert.butoxycarbonyl or tert.amyloxycarbonyl.

A C$_1$–C$_6$ alkylene chain is preferably a C$_1$–C$_3$ alkylene chain, such as a —CH$_2$—, —(CH$_2$)$_2$—, —(CH$_2$)$_3$—,

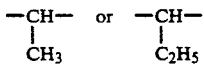

chain.

A di(C$_1$–C$_6$ alkyl)amino group is preferably a di(C$_1$–C$_4$ alkyl)amino group, in particular a di(C$_1$ or C$_2$ alkyl)amino group.

a

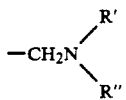

group,
wherein R' and R" taken together with the nitrogen atom form a heterocyclic ring, is preferably a morpholinomethyl, a thiomorpholinomethyl or a N-piperazinyl-methyl group, wherein said heterocyclic rings may be unsubstituted or substituted by C$_1$–C$_4$ alkyl.

The asymmetric carbon atom to which the R$_c$ group is linked may have either the R or S configuration. The side-chain of an α-aminoacid is specifically the residue obtained from an α-aminoacid by removing the amino and the carboxy groups together with the α-carbon atom to which they are linked. The side-chain of an α-aminoacid as defined above is preferably the side-chain deriving from a naturally occurring aminoacid.

Examples of such aminoacids are alanine, valine, leucine, isoleucine, phenylalanine, proline, hydroxyproline, serine, thereonine, cysteine, cystine, methionine, tryptophan, tyrosine, asparagine, glutamine, aspartic acid, glutamic acid, lysine, arginine, histidine and phenylserine. Preferred examples of said chains of the above mentioned aminoacids are —CH$_3$ (deriving from alanine), —CH$_2$—CH(CH$_3$)$_2$ (deriving from leucine) and —CH$_2$—C$_6$H$_5$ (deriving from phenylalanine).

Examples of pharmaceutically acceptable salts of the compounds of formula (I) are either those with inorganic bases, such as sodium, potassium, calcium and aluminium hydroxides, or with organic bases, such as lysine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

Suitable compounds of formula (I) for use in the invention include in particular the following compounds which are described in our above identified European, British and International patent applications:

2-cyano-3-(1,4-dihydro-1-phenyl-[1]-benzothiopyrano[4,3-c] pyrazol-3-yl)-3-oxo-N-phenyl-propanamide;

N-benzyl-2-cyano-3-(1,4-dihydro-1-phenyl-[1]-benzothiopyrano [4,3-c]pyrazol-3-yl)-3-oxo-propanamide;

2-cyano-N-(4-fluoro-phenyl)-3-(1,4-dihydro-1-phenyl-[1]-benzothiopyrano[4,3-c]pyrazol-3-yl)-3-oxo-propanamide;

2-cyano-N-(4-fluoro-phenyl)-3-[1-(4-fluoro-phenyl)-4,-dihydro-[1]-benzothiopyrano[4,3-c]pyrazol-3-yl]-3-oxopropanamide;

2-cyano-3-(1,4-dihydro-8-methyl-1-phenyl-[1]-benzothiopyrano [4,3-c]pyrazol-3-yl)-3-oxo-N-phenyl-propanamide;

3-(8-chloro-1,4-dihydro-1-phenyl-[1]-benzothiopyrano[4,3-c] pyrazol-3-yl)-2-cyano-3-oxo-N-phenyl-propanamide;

3-(6-amino-1,4-dihydro-1-phenyl-[1]-benzothiopyrano[4,3-c] pyrazol-3-yl)-2-cyano-3-oxo-N-phenyl-propanamide;

N-(3-chloro-phenyl)-2-cyano-3-(1,4-dihydro-1-phenyl-[1]-benzothiopyrano[4,3-c]pyrazol-3-yl)-3-oxo-propanamide;

2-cyano-3-(1,5-dihydro-1-phenyl-[2]-benzothiopyrano[4,3-c] pyrazol-3-yl)-3-oxo-N-phenyl-propanamide;

2-cyano-3-(4,5-dihydro-1-phenyl-[1]-benz[g]indazol-3-yl)-3-oxo-N-phenyl-propanamide;

2-cyano-3-(8-ethoxylylamino-1,4-dihydro-1-phenyl-[1-benzothiopyrano[4,3-c]pyrazol-3-yl)-3-oxo-N-phenyl-propanamide;

2-cyano-3-(1,4-dihydro-1-phenyl-[1]-benzothiopyrano[4,3-c]pyrazol-3-yl)-N-(3-nitro-phenyl)-3-oxo-propanamide;

2-cyano-3-(1,4-dihydro-1-phenyl-[1]-benzothiopyrano[4,3-c]pyrazol-3-yl)-3-yl)-3-oxo-N-(3-trifluoromethyl-phenyl)-propanamide; 3-(7-tert.butyl-1,4-dihydro-1-phenyl-indeno[1,2-c]pyrazol-3-yl)-2-cyano-3-oxo-N-phenyl-propanamide;

2-cyano-3-(7-fluoro-1,4-dihydro-1-phenyl-indeno[1,2-c]pyrazol-3-yl)-3-oxo-N-phenyl-propanamide;

2-cyano-N-(4-fluoro-phenyl)-3-(7-fluoro-1,4-dihydro-1-phenyl-indeno[1,2-c]pyrazol-3-yl-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

3-(6-tert.butoxycarbonyl-1,4-dihydro-1-phenyl-[1]-benzothiopyrano[4,3-c]pyrazol-3-yl)-2-cyano-3-oxo-N-phenyl-propanamide;

3-(5-tert.butoxycarbonyl-1,4-dihydro-1-phenyl-indeno[1,2-c]pyrazol-3-yl)-2-cyano-3-oxo-N-phenyl-propanamide;

2-cyano-3-(1,4-dihydro-7-morpholinomethyl-1-phenyl-indeno [1,2-c]pyrazol-3-yl)-3-oxo-N-phenyl-propanamide;

2-cyano-3-(1,4-dihydro-5-morpholinomethyl-1-phenyl-indeno [1,2-c]pyrazol-3-yl)-3-oxo-N-phenyl-propanamide;

2-cyano-3-(8-fluoro-1,4-dihydro-6-morpholinomethyl-1-phenyl-[1]-benzopyrano[4,3-c]pyrazol-3-yl)-3-oxo-N-phenyl-propanamide;

2-cyano-3-(1,4-dihydro-8-morpholinomethyl-1-phenyl-[1]-benzo-pyrano[4,3-c]pyrazol-3-yl)-3-oxo-N-phenyl-propanamide; 2-cyano-3-(1,4-dihydro-6-N,N-dimethylaminoethoxycarbonyl-1-phenyl-[1]-benzothiopyrano[4,3-c]pyrazol-3-yl)-3-oxo-N-phenyl-propanamide;

3-(6-carboxy-1,4-dihydro-1-phenyl-[1]-benzothiopyrano[4,3-c] pyrazol-3-yl)-2-cyano-3-oxo-N-phenyl-propanamide;

3-(5-carboxy-1,4-dihydro-1-phenyl-indeno[1,2-c]pyrazol-3-yl)-2-cyano-3-oxo-N-phenyl-propanamide;

2-cyano-3-(1,4-dihydro-1-phenyl-indeno[1,2-c]pyrazol-3-yl)-3-oxo-N-phenyl-propanamide;

2-cyano-N-(4-fluoro-phenyl)-3-[1-(4-fluoro-phenyl)-1,4-dihydro-indeno[1,2-c]pyrazol-3-yl]-3-oxo-propanamide;

2-cyano-N-(4-fluoro-phenyl)-3-(1,4-dihydro-1-phenyl-indeno [1,2-c]pyrazol-3-yl)-3-oxo-propanamide;

N-(3-chloro-phenyl)-2-cyano-3-(1,4-dihydro-1-phenyl-indeno [1,2-c]pyrazol-3-yl)-3-oxo-propanamide;

2-cyano-3-(1,4-dihydro-7-methyl-1-phenyl-indeno[1,2c] pyrazol-3-yl)-3-oxo-N-phenyl-propanamide;

2-cyano-3-oxo-(1-phenyl-1H-benzothieno[3,2-c]pyrazol-3-yl)-N-phenyl-propanamide;

3-(8-carboxy-1,4-dihydro-1-phenyl-[1]-benzopyrano[4,3c] pyrazol-3-yl)-2-cyano-3-oxo-N-phenyl-propanamide;

2-cyano-3-(1,4-dihydro-1-phenyl-[1]-benzopyrano[4,3c] pyrazol-3-yl)-3-oxo-N-phenyl-propanamide;

3-(8-amino-1,4-dihydro-1-phenyl-[1]-benzothiopyrano[4,3-c] pyrazol-3-yl)-2-cyano-3-oxo-N-phenyl-propanamide; and the pharmaceutically acceptable salts thereof, in particular the sodium and the potassium salts. The compounds of formula (I) and the salts thereof can be prepared by a process comprising:

a) reacting a compound of formula (II)

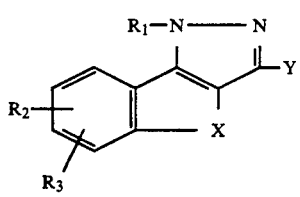

wherein
X, $R_1$, $R_2$ and $R_3$ are as defined above and Y is carboxy or a reactive derivative of a carboxy group, with a compound of formula (III)

wherein
Q' is as Q defined above, except carboxy, so obtaining a compound of formula (I), wherein Q is as defined above except carboxy; or b) reacting a compound of formula (IV)

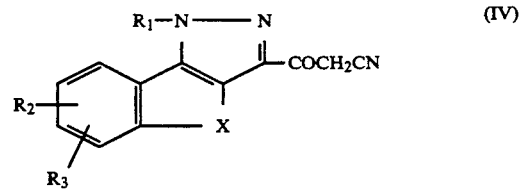

wherein
X, $R_1$, $R_2$ and $R_3$ are as defined above, with a compound formula (V)

$$R_b-N=C=O \qquad (V)$$

wherein
$R_b$ is as defined above, so obtaining a compound of formula (I) wherein Q is a -CONHR$_b$ group, wherein R$_b$ is as defined above; or c) reacting a compound of formula (IV)

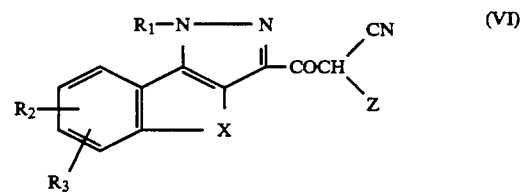

wherein
X, $R_1$, $R_2$ and $R_3$ are defined above and Z is a reactive derivative of a carboxy group, with a compound of formula (VII)

wherein
$R_a$ and $R_b$ are as defined above, so obtaining a cmpound of formula (I) wherein
Q is a

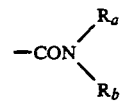

group
wherein $R_a$ and $R_b$ are as defined above; or d) hydrolysing a compound of formula (I), wherein Q is a
$C_2$-$C_7$ alkoxycarbonyl or

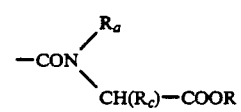

group
in which $R_a$ and
$R_c$ are as defined above and R is $C_1$-$C_6$ alkyl, so as to obtain the corresponding compound of formula (I), wherein Q is a free carboxy group or a

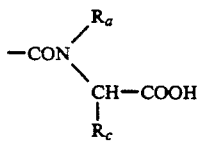

group in which $R_a$ and $R_c$ are as defined above; and, if desired, converting a compound of formula (I) into another cmpound of formula (I) and/or, if desired, converting a compound of formula (I) into a pharmaceutically acceptable salt and/or, if desired, converting a salt into a free compound, and/or, if desired, separating a mixture of isomers of a compound of formula (I), into the single isomers.

The details inherent to the methods of preparation are described in the above-identified European, International and British patent applications, the disclosures of which are incorporated herein by reference. Surprisingly, as stressed above, we have now found that the compounds of formula (I), here above described, and their salts are effective in stimulating myelopoiesis in bone marrow suppressed mammals, including humans.

Conditions wherein suppressed myelopoiesis occurs, thus creating a life-threatening state, and wherein the use of a compound of formula (I), as herein defined, or a pharmaceutically acceptable salt thereof is of benefit in stimulating myelopoiesis are for example the case of cancer chemotherapy and cancer radiation therapy; immunosuppressant therapy used for organ or tissue transplantation; immunosuppressant therapy in the case of an autoimmune disease; the case of autologous and allogenic bone marrow transplants; the case of severe burns, the case of accidental exposure to radiation or to certain chemicals, e.g. benzene, and the case of asplastic anemia, myelodysplastic syndrome and congenital or acquired bone marrow disorders.

Particular cases of cancer chemotherapy in which the compounds of formula (I), here above described are useful in stimulating myelopoiesis are, for example, those in which the chemotherapeutic treatment is carried out by administration of one or more products chosen for example from the group of alkylating agents, e.g. cyclophosphamide, iphosphamide and chlorambucil, antibiotics, e.g. actinomycin D and mitomycin, anthracycline antibiotics, e.g. daunorubicin and doxorubicin, antimetabolites, e.g. 5-fluororacil, methotrexate and 6-mercaptopurine vincaalkaloids, e.g. vinblastine and vincristine, and platinum complexes, e.g. cis-platin and carboplatin.

Particular cases of immunosuppressant therapy in which the the compounds of formula (I), here above described, are useful in stimulating myelopoiesis are, for example, those in which the immunosuppressant treatment is carried out by administration of cyclophosphamide, azathioprine, 6-mercaptopurine, methotrexate and corticosteroids.

Preferred cases of organ transplants treated by immunosuppressant therapy, in which the compounds of formula (I), here above described, are useful in stimulating myelopoiesis are, for example, the cases of heat kidney and bone marrow transplants.

Preferred cases of autoimmune diseases, treated by immunosuppressant therapy, in which the compounds of formula (I), here above described, are useful in stimulating myelopoiesis are, for example, the cases of rheumatoid arthritis, systemic lupus erythematosus, juvenile diabetes, ulcerative colitis, glomerulonephritis and multiple sclerosis.

The myelopoiesis stimulating activity of the compounds of formula (I) is proved, for example, by the fact that they are effective in accelerating the recovery of the total cound of circulating leukocytes in immunosuppressed animals, as it comes out, for example, from the experimental data herein afterwards reported. Indeed, for instance the biological data set out in the Tables of the Examples herein provided show clearly that a therapy with a representative group of compounds according to the present invention accelerates leukocytes recovery in cyclophosphamide treated mice.

A further object of the present invention is to provide a method of treatment of a disease having autoimmune basis by combined administration of (1) a pharmaceutical composition containing a compound of formula (I), as herein defined, or a pharmaceutically acceptable salt thereof and (2) a pharmaceutical composition containing an effective amount of an immunosuppressant agent.

Examples of diseases having auto-immune basis, which can be treated by the method of therapy, according to the present invention, are rheumatoid arthritis, systemic lupus erythematosus, juvenile diabetes, autoimmune haemolytic anaemia, ulcerative colitis, idiopathic thrombocytopenic purpura, active chronic hepatitis, glomerulonephritis and multiple sclerosis.

Examples of immunosuppressant agents which can be used according to the method of treatment provided by the present invention includes cyclophosphamide, azathioprine, 6-mercaptopurine, methotrexate and corticosteroids. The term "combined" administration according to the method of treatment provided by the present invention is meant to include both separate and substantially contemporaneous administration of a pharmaceutical composition containing a compound of formula (I), as herein defined, or a pharmaceutically acceptable salt thereof and of a pharmaceutical composition containing an effective amount of an immunosuppressant agent. The separate treatment with a compound of formula (I), or a pharmaceutically acceptable salt thereof, can commence prior, e.g. one or two days, to immunosuppressant treatment or subsequent, e.g. one or two days, to commencement of immunosuppressant treatment. Doses of immunosuppressant agent to be administered in practicing the method of the invention will of course vary depending upon, e.g., the mode of administration and the condition to be treated.

In general, amounts administered will be of the same order to those conventionally employed in immunosuppressant therapy.

In view of their high biological activity and low toxicity the compounds of the invention can be safely used in medicine.

For example, the approximate acute toxicity ($LD_{50}$) in the mouse of the compounds 2-cyano-3-(1,4-dihydro-1-phenyl-[1]-benzopyrano[4,3-c]pyrazol-3-yl)-3-oxo-N-phenylpropanamide, and 2-cyano-3-(1,4-dihydro-1-phenyl-[1]-benzothiopyrano [4,3-c] pyrazol-3-yl)-3-oxo-N-phenyl-propanamide, determined per os with single administration of increasing doses and measured on the seventh day after the day of treatment, is higher than 800 mg/kg. Analogous toxicity data have been found for the other compounds of formula (I).

As preferred examples of compounds useful in stimulating myelopoiesis in bone marrow suppressed mammals, the following can be mentioned: 2-cyano-3-(1,4-dihydro-1-phenyl-[1]-benzothiopyrano[4,3-c] pyrazol-3-yl)-3-oxo-N-phenyl-propanamide (internal code FCE 24578), 2-cyano-3-(1,4-dihydro-1-phenyl-indeno[1,2-c]pyrazol-3-yl)-3-oxo-N-phenyl-propanamide (internal code FCE 25276), 2-cyano-N-(4-fluoro-phenyl)-3-[1-(4-fluoro-phenyl)1,4-dihydro-[1]-benzothiopyrano [4,3-c]pyrazol-3-yl]-3-oxopropanamide (internal code FCE 25611) and 2-cyano-N-(4-fluorophenyl)-3-[1-(4-fluorophenyl)-1,4-dihydro-indeno[1,2-c]pyrazol3-yl)-3-oxo-propanamide (internal code FCE 26317). The therapeutic regimen for the different pathological conditions must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute syndromes. For maintenance regimens the oral or parenteral, e.g. intramuscular or subcutaneous, route is preferred. For these purposes the compounds of the invention, for example 2-cyano-3-(1,4-dihydro-1-phenyl-[1]-benzothiopyrano[4,3-c] pyrazol-3-yl)-3-oxo-N-phenyl-propanamide (internal code FCE 24578) and 2-cyano-3-(1,4-dihydro-1-phenyl-indeno[1,2-c]pyrazol-3-yl)-3-oxo-N-phenyl-propanamide (internal code FCE 25276), can be administered orally at doses ranging e.g. from about 0.5 to about 10 mg/kg of body weight per day in adult humans. Doses of active compounds ranging e.g. from about 0.2 to about 5 mg/kg of body weight can be used for the parenteral administration in adult humans. Of course, these dosage regimens may be adjusted to provide the optimal therapeutic response. The present invention also refers, in another aspect, to pharmaceutical compositions suitable for stimulating myelopoiesis in bone marrow suppressed mammals, including humans, comprising a compound of formula (I), as defined above, in association with a pharmaceutically acceptable excipient (which can be a carrier or diluent). The nature of the pharmaceutical compositions containing the compounds of formula (I) in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions or suspension, tablets, pills, gelatine capsules, syrups, drops or suppositories. Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes. The liquid dispersions for oral administration may be e.g. syrups, emulsions and suspensions. The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, sesame oil, miglyol, ethyl oleate, glycols, e.g. propylene glycol, and one or more customary ingredients according to the pharmaceutical formulation techniques, and if desired, a suitable amount of lidocaine hydrochloride. The solutions for intravenous injections or infusions may contain as carrier, for example, sterile water or preferably they may be in the form of sterile aqueous isotonic saline solutions. The suppositories may contain together with the active compound a pharmaceutically acceptable carrier, e.g. cocoa-butter, polyethylene glycol, a polyoxyethylene sorbitan fatty acid ester surfactant or lecithin. Preferred compounds of formula (I), suitable for stimulating myelopoiesis in bone marrow suppressed mammals, including humans, are the compounds of formula (I) wherein X represents:

a) a $-S(O)_n-$ group wherein n is as defined above;
b) a $-CH(R_6)$-group wherein $R_6$ represents hydrogen or $C_1$ or $C_2$alkyl;
c) a

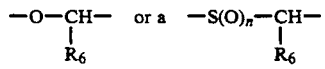

group
wherein n and $R_6$ are as defined above; or
d) a

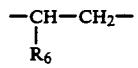

group,
wherein $R_6$ is as defined above;
$R_1$ represent $C_1-C_4$ alkyl or phenyl, the phenyl being unsubstituted or substituted by a substituent chosen from halogen, trifluoromethyl, $C_1-C_6$ alkyl and $C_1-C_6$ alkoxy; $R_2$ represents:
a) hydrogen, halogen, $C_1-C_4$ alkyl or $C_1-C_4$ alkoxy;
b) nitro, amino, formylamino or $C_2-C_4$ alkanoylamino;
c) di($C_1$ or $C_2$ alkyl)amino or a

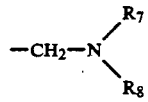

group, wherein each
of $R_7$ and $R_8$ independently is $C_1-C_4$ alkyl or $R_7$ and $R_8$, taken together with the nitrogen atom to which they are linked, form a heterocyclic ring which is selected from N-pyrrolidinyl, N-piperazinyl, morpholino, thiomorpholino and piperidino and which is unsubstituted or substituted by $C_1$-$C_4$ alkyl;
d) —$CH_2OH$, —COOH or $C_2$-$C_7$ alkoxycarbonyl;
e) a

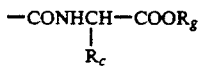

group,
wherein $R_g$ is hydrogen or $C_1$-$C_4$ alkyl and $R_c$ is as defined above;
f) a —$CH_2OCO(CH_2)_nCOOR_f$ or a —$NHCO(CH_2)_nCOOR_f$ group, wherein n is as defined above and $R_f$ is hydrogen or $C_1$-$C_4$ alkyl;
g) $C_2$-$C_7$ alkoxycarbonyl substituted by a

group,
wherein
$R_7$ and $R_8$ are as defined above;
$R_3$ is as $R_2$ defined above under a);
Q represents hydrogen or a

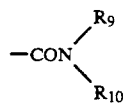

group
wherein $R_9$ represents hydrogen or $C_1$-$C_6$ alkyl and $R_{10}$ represents $C_1$-$C_{10}$ alkyl, a

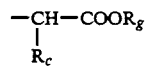

group wherein $R_c$ and $R_g$ are as defined above or a

—(A')$_m$-$R_{11}$ group wherein m is as defined above, A' is a $C_1$-$C_3$ alkylene chain and $R_{11}$ is:
a) pyridyl, unsubstituted or substituted by a substituent chosen from halogen, $C_1$ or $C_2$ alkyl and $C_1$ or $C_2$ alkoxy;
b) phenyl, unsubstituted or substituted by one or two substituents independently chosen from halogen, $CF_3$, $C_1$-$C_4$ alkyl, $C_1$-$C_4$ alkoxy, amino, nitro, formylamino, $C_2$-$C_4$ alkanoylamino and di($C_1$-$C_4$ alkyl)amino;
c) phenyl substituted by $C_2$-$C_7$ alkoxycarbonyl or by a

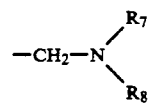

group,
wherein $R_7$ and $R_8$ are as defined above, and optionally by another substituent chosen from halogen, $C_1$-$C_4$ alkyl and $C_1$-$C_4$ alkoxy;
d) 2-thienyl or 2-furyl;
e) a heterocyclic ring which is selected from 2-pyrimidyl, 2-thiazolyl and 3-isoxazolyl and which is unsubstituted or substituted by $C_1$ or $C_2$ alkyl;
and the pharmaceutically acceptable salts thereof.

Further preferred compounds of formula (I) are those in which X represents:
a') a sulphur atom;
b') a

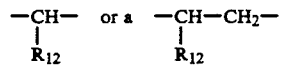

group
wherein $R_{12}$ is hydrogen or methyl; or
c') a

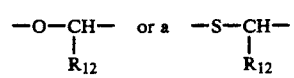

group,
wherein $R_{12}$ is as defined above;
$R_1$ represents phenyl unsubstituted or substituted by a substituent chosen from halogen, trifluoromethyl and $C_1$-$C_4$-alkyl;
$R_2$ represents:
a') hydrogen, halogen, $C_1$-$C_4$ alkyl, $C_1$-$C_4$ alkoxy, amino or a

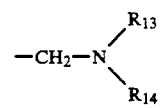

group,
wherein each of $R_{13}$ and $R_{14}$ independently is $C_1$-$C_4$ alkyl or $R_{13}$ and $R_{14}$, taken together with the nitrogen atom to which they are linked, form a heterocyclic ring which is selected from N-pyrrolidinyl, N-piperazinyl, morpholino, thiomorpholino and piperidino and which is unsubstituted or substituted by methyl;
b') —COOH, $C_2$-$C_7$ alkoxycarbonyl or a

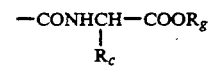

group,
wherein $R_g$ is hydrogen or $C_1$-$C_4$ alkyl and $R_c$ is hydrogen, phenyl or the side-chain of an α-aminoacid;
c') a —$NHCO(CH_2)_nCOOR_g$ group, wherein n is as defined above and $R_g$ is hydrogen or $C_1$-$C_4$ alkyl;
d') a $C_2$-$C_7$ alkoxycarbonyl group substituted by a

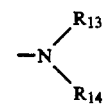

group,
wherein $R_{13}$ and $R_{14}$ are as defined above; $R_3$ represents hydrogen, halogen or $C_1$-$C_4$ alkyl;
Q represents hydrogen or a

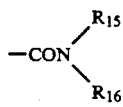

group wherein $R_{15}$ is hydrogen or $C_1$–$C_2$ alkyl and $R_{16}$ is $C_1$–$C_6$ alkyl, a

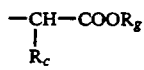

group, wherein $R_g$ is hydrogen or $C_1$–$C_4$ alkyl and $R_c$ is as defined above, or a —(A')$_m$–$R_{17}$ group wherein m is zero or 1, A' is a $C_1$–$C_3$ alkylene chain and $R_{17}$ is:

a") unsubstituted pyridyl; or phenyl unsubstituted or substituted by a substituent chosen from halogen, $CF_3$, $C_1$–$C_2$ alkyl, $C_1$–$C_2$ alkoxy, nitro, di($C_1$–$C_2$ alkyl)amino and a

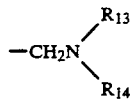

group, wherein $R_{13}$ and $R_{14}$ are as defined above;

b") 2-thienyl or 2-furyl; or c") a heterocyclic ring which is selected from 2-thiazolyl or 3-isoxazolyl and which is unsubstituted or substituted by methyl; and the pharmaceutically acceptable salts thereof.

In particular preferred compounds of formula (I) are those in which X represents:

a''') a sulphur atom or a —$CH_2$— or —$CH_2$—$CH_2$— group; or b''') a —O—$CH_2$— or a —S—$CH_2$— group;

$R_1$ represents phenyl unsubstituted or substituted by halogen;

$R_2$ represents hydrogen, halogen, $C_1$–$C_4$ alkyl, $C_2$–$C_7$ alkoxycarbonyl or a

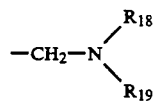

group, wherein $R_{18}$ and $R_{19}$, taken together with the nitrogen atom to which they are linked form a heterocyclic ring which is selected from N-piperazinyl, morpholino and thiomorpholino and which is unsubstituted or substituted by methyl;

$R_3$ represents hydrogen, halogen or $C_1$–$C_4$ alkyl;

Q represents a —CONH—(A")$_m$–$R_{20}$ group wherein m is zero or 1, A" is a $C_1$–$C_2$ alkylene chain and $R_{20}$ is phenyl unsubstituted or substituted by a substituent chosen from halogen, nitro and trifluoromethyl; and the pharmaceutically acceptable salts thereof.

Specific examples of preferred compounds of formula (I), suitable for treating autoimmune disease, are the following ones:

2-cyano-3-(1,4-dihydro-1-phenyl-[1]-benzothiopyrano[4,3-c] pyrazol-3-yl)-3-oxo-N-phenyl-propanamide;

N-benzyl-2-cyano-3-(1,4-dihydro-1-phenyl-[1]-benzothiopyrano [4,3-c]pyrazol-3-yl)-3-oxo-propanamide;

2-cyano-N-(4-fluoro-phenyl)-3-(1,4-dihydro-1-phenyl-[1]-benzothiopyrano[4,3-c]pyrazol-3-yl)-3-oxo-propanamide; 2-cyano-N-(4-fluoro-phenyl)-3-[1-(4-fluoro-phenyl)-1,4-dihydro-[1]-benzothiopyrano[4,3-c]pyrazol-3-yl]-3-oxopropanamide;

2-cyano-3-(1,4-dihydro-8-methyl-1-phenyl-[1]-benzothiopyrano [4,3-c]pyrazol-3-yl]-3-oxo-N-phenyl-propanamide;

3-(8-chloro-1,4-dihydro-1-phenyl-[1]-benzothiopyrano[4,3-c] pyrazol-3-yl)-2-cyano-3-oxo-N-phenyl-propanamide;

N-(3-chloro-phenyl)-2-cyano-3-(1,4-dihydro-1-phenyl-[1]-benzothiopyrano[4,3-c]pyrazol-3-yl)-3-oxo-propanamide;

2-cyano-3-(1,4-dihydro-1-phenyl-indeno[1,2-c]pyrazol-3-yl)-3-oxo-N-phenyl-propanamide;

2cyano-N-(4-fluoro-phenyl)-3-[1-(4-fluoro-phenyl)-1,4-dihydro-indeno[1,2-c]pyrazol-3-yl]-3-oxo-propanamide; 2-cyano-N-(4-fluoro-phenyl)-3-(1,4-dihydro-1-phenyl-indeno [1,2]pyrazol-3-yl)-3-oxo-propanamide;

N-(3-chloro-phenyl)-2-cyano-3-(1,4-dihydro-1-phenyl-indeno [1,2-c]pyrazol-3-yl)-3-oxo-propanamide;

2-cyano-3-(1,4-dihydro-1-phenyl-[1]-benzopyrano[4,3-c] pyrazol-3-yl)-3-oxo-N-phenylpropanamide;

2-cyano-3-(1,4-dihydro-7-methyl-1-phenyl-indeno[1,2-c] pyrazol-3-yl)-3-oxo-N-phenyl-propanamide;

3-(7-tert.butyl-1,4-dihydro-1-phenyl-indeno[1,2-c]pyrazol-3-yl)-2-cyano-3-oxo-N-phenyl-propanamide;

2-cyano-3-(7-fluoro-1,4-dihydro-1-phenyl-indeno[1,2-c] pyrazol-3-yl)-3-oxo-N-phenyl-propanamide;

2-cyano-N-(4-fluoro-phenyl)-3-(7-fluoro-1,4-dihydro-1-phenyl-indeno[1,2-c]pyrazol-3-yl)-3-oxo-propanamide;

3-(7-tert.butyl-1,4-dihydro-1-phenyl-indeno[1,2-c]pyrazol-3-yl)-2-cyano-N-(4-fluoro-phenyl)-3-oxo-propanamide;

2-cyano-N-(4-fluoro-phenyl)-3-(1,4-dihydro-7-methyl-1-phenylindeno[1,2-c]pyrazol-3-yl)-3-oxo-propanamide;

3-(6-tert.butoxycarbonyl-1,4-dihydro-1-phenyl-[1]-benzothiopyrano[4,3-c]pyrazol-3-yl)-2-cyano-3-oxo-N-phenyl-propanamide; 31-(5-tert.butoxycarbonyl-1,4-dihydro-1-phenyl-indeno[1,2-c]pyrazol-3-yl)-2-cyano-3-oxo-N-phenyl-propanamide;

2-cyano-3-(1,4-dihydro-5-morpholinomethyl-1-phenyl-indeno [1,2-c]pyrazol-3-yl)-3-oxo-N-phenyl-propanamide; 2-cyano-3-(8-fluoro-1,4-dihydro-6-morpholinomethyl-1-phenyl-[1]-benzopyrano[4,3-c]pyrazol-3-yl)-3-oxo-N-phenyl-propanamide; and the pharmaceutically acceptable salts thereof, in particular the sodium and the potassium salts.

The following examples illustrate but do not limit the present invention.

EXAMPLE 1

Recovery of the Total Count of Circulating Leukocytes in Cyclophosphamide Immunosuppressed mice Groups of 4 mice were injected once with the powerful bone marrow suppressant cyclophosphamide (CPA), at the dose of 200 mg/kg i.p.

Beginning on the day after CPA injection and up to the day before the sacrifice, the mice were injected i.p. with the vehicle (5% methocel) or the test compound suspended in 5% methocel at the doses of 10 mg/kg. Periferal blood was drawn from the retroorbital plexus at different times after CPA treatment and total leukocytes were counted in a Bürker's hemocytometer.

Following Table I summarizes the test data obtained for a representative compound of formula (I) according to the present invention, i.e. 2-cyano-3-(1,4-dihydro-1-phenyl-[1]-benzothiopyrano[4,3-c]pyrazol-3-yl)-3-oxo-N-phenyl -propanamide (internal code FCE 24578).

TABLE I

Recovery of the total count of circulating leukocytes in cyclophosphamide immunodepressed mice by FCE 24578 therapy.

| Treatment | days | Total leukocytes cells/mm$^3$ ± S.E.[o] |
| --- | --- | --- |
| FCE 24578 | +4 | 3100 ± 400** |
| 10 mg/kg | +5 | 11700 ± 200** |
| | +6 | 10400 ± 1800** |
| | +7 | 10300 ± 2300** |
| | +9 | 16600 ± 2800** |
| vehicle | +4 | 1300 ± 150 |
| | +5 | 3700 ± 500 |
| | +6 | 3800 ± 700 |
| | +7 | 6800 ± 700 |
| | +9 | 6500 ± 700 |

[o]Arithmetic mean from four mice ± Standard error.
** = P < 0.01 vs. vehicle treated mice (Dunnett's "t" test)

EXAMPLE 2

Recovery of the Total Count of Circulating Leukocytes in Cyclophosphamide Immunodepressed Mice Groups of 3 mice were injected once with cyclophamide (CPA) at the dose of 200 mg/kg i.p. Beginning on the day after CPA injection and for five consecutive days (from the day+1 up to the day+5), the mice were injected i.p. with the vehicle (5% Methocel) or with the test compound, suspended in 5% Methocel, at the dose of 10 mg/kg.

Peripheral blood was drawn from the retrooribtal plexus at different times after CPA treatment and total leukocytes were counted in a Bürker's hemocytometer. Following Table II summarizes the test data obtained for the following representative compounds of formula (I) according tot he present invention;

2-cyano-N-(4-fluoro-phenyl)-3-[1-(4-fluoro-phenyl)-1,4-dihydro-indeno[1,2-c]pyrazol-3-yl]-3-oxo-propanamide (internal code FCE 26317);

2-cyano-3-(7-fluoro-1,4-dihydro-1-phenyl-indeno[1,2-c]pyrazol-3-yl)-3-oxo-N-phenyl-propanamide (internal code FCE 26676); and 2-cyano-3-(1,4-dihydro-1-phenyl-[1]-benzothiopyrano[4,3-c] pyrazol-3-yl)-3-oxo-N-phenylpropanamide (internal code FCE 24578).

TABLE II

Recovery of the total count of circulating leukocytes in CPA immunodepressed mice by treatment with compounds FCE 26317, FCE 26676 and FC 24578.

| Treatment | Total leukocytes-cells/mm$^3$ ± S.E.[o] | | |
| --- | --- | --- | --- |
| | +5[oo] | +6 | +7 |
| FCE 26317 | 3188 ± 399** | 5977 ± 815** | 9566 ± 422** |
| FCE 26676 | 1777 ± 408 | 6066 ± 1213** | 9233 Y 1360** |
| FCE 24578 | 3433 ± 546** | 8977 ± 1364** | 6522 ± 792 |

TABLE II-continued

Recovery of the total count of circulating leukocytes in CPA immunodepressed mice by treatment with compounds FCE 26317, FCE 26676 and FC 24578.

| Treatment | Total leukocytes-cells/mm$^3$ ± S.E.[o] | | |
| --- | --- | --- | --- |
| | +5[oo] | +6 | +7 |
| Vehicle | 900 ± 97 | 1600 ± 164 | 4722 ± 754 |

[o]Arithmetic mean from three mice ± standard error.
[oo]Days after CPA injection.
**P < 0.01 vs controls (Dunnett's "t" test).

EXAMPLE 3

Recovery of the Total Count of Circulating Leukocytes in Cyclophophamide Immunosuppressed Mice By proceeding according to the schedule of treatment described in the Example 2, the following representative compounds of formula (I) according to the present invention were evaluated in the title biological test:

2-cyano-3-(1,4-dihydro-1-phenyl-[1]-benzopyrano[4,3-c]pyrazol-3-yl)-3-oxo-N-phenyl-propanamide (internal code FCE 25158);

2-cyano-3-(1,4-dihydro-1-phenyl-indeno[1,2-c]pyrazol-3-yl)-3-oxo-N-phenyl-propanamide (internal code FCE 25276);

N-benzyl-2-cyano-3-(1,4-dihydro-1-phenyl-[1]-benzothiopyrano [4,3-c]pyrazol-3-yl)-3-oxo-propanamide (internal code FCE 25324); and 2-cyano-3-(1,4-dihydro-1-phenyl-[1]-benzothiopyrano[4,3-c] pyrazol-3-yl)-3-oxo-N-phenyl-propanamide (internal code FCE 24578). The test data obtained are summarized in the following Table III.

TABLE III

Recovery of the total count of circulating leukocytes in CPA immunodepressed mice by treatment with compounds FCE 25158, FCE 25276, FCE 25324 FC 24578.

| Treatment | Total leukocytes-cells/mm$^3$ ± S.E.[o] | | |
| --- | --- | --- | --- |
| | +5[oo] | +6 | +7 |
| FCE 25158 | 1666 ± 170 | 5466 ± 887* | 8088 ± 290** |
| FCE 25276 | 3811 ± 248** | 8477 ± 970** | 7033 ± 292** |
| FCE 25324 | 1955 ± 198** | 6044 ± 1381** | 5244 ± 178* |
| FCE 24578 | 2011 ± 108** | 6855 ± 419** | 7022 ± 492** |
| Vehicle | 988 ± 141 | 1933 ± 305 | 2744 ± 579 |

[o]Arithmetic mean from three mice ± Standard error.
[oo]Days after CPA injection.
*P < 0.05 vs controls (Dunnett's "t" test)
***P < 0.01 vs controls (Dunnett's "t" test).

EXAMPLE 4

Recovery of the total count of circulating leukocytes in cyclophophamide immunodepressed mice By proceeding according to the schedule of treatment described in the Example 2, the following representative compounds of formula (I) according to the present invention were evaluated in the title biological test:

2-cyano-3-(1,4-dihydro-7-methyl-1-phenyl-indeno[1,2-c]pyrazol-3-yl)-3-oxo-N-phenyl-propanamide (internal code FCE 26418); and 2-cyano-3-(1,4-dihydro-1-phenyl-[1]-benzothiopyrano[4,3-c] pyrazol-3-yl)-3-oxo-N-phenyl-propanamide (internal code FCE 24578).

The test data obtained are summarized in the following Table IV.

TABLE IV

Recovery of the total count of circulating leukocytes in CPA immunodepressed mice by treatment with compounds FCE 26418 and FC 24578.

| Treatment | Total leukocytes-cells/mm$^3$ ± S.E.$^o$ | | |
|---|---|---|---|
| | +5$^{oo}$ | +6 | +7 |
| FCE 26418 | 1963 ± 504** | 5600 ± 593** | 7233 ± 105** |
| FCE 24578 | 2780 ± 327** | 7511 ± 1008** | 5300 ± 417 |
| Vehicle | 692 ± 82 | 1255 ± 142 | 3266 ± 465 |

$^o$Arithmetic mean from three mice ± Standard error.
$^{oo}$Days after CPA injection.
**P < 0.01 vs controls (Dunnett's "t" test).

FORMULATION EXAMPLES

Formulation 1: Tablets

Tablets, each weighing 150 mg and containing 50 mg of the active substance are manufactured as follows:

| Composition (for 10000 tablets) | |
|---|---|
| 2-cyano-3-(1,4-dihydro-1-phenyl-[1]-benzothiopyrano[4,3-c]pyrazol-3-yl)-3-oxo-N-phenyl-propanamide | 500 g |
| Lactose | 710 g |
| Corn starch | 238 g |
| Talc powder | 36 g |
| Magnesium stearate | 16 g |

22-cyano-3-(1,4-dihydro-1-phenyl-[1]-benzothiopyrano[4,3-c]pyrazol-3-yl)-3-oxo-N-phenyl-propanamide, lactose and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

| Formulation 2: Capsules (50 mg) | |
|---|---|
| 2-cyano-3-(1,4-dihydro-1-phenyl-[1]-benzothiopyrano[4,3-c]pyrazol-3-yl)-3-oxo-N-phenyl-propanamide | 50 mg |
| Lactose | 298 mg |
| Corn starch | 50 mg |
| Magnesium stearate | 2 mg |
| Total | 400 mg |

Encapsulate in two-piece hard gelatin capsules.

| Formulation 3: Suppository (100 mg) | |
|---|---|
| 2-cyano-3-(1,4-dihydro-1-phenyl-[1]-benzothiopyrano[4,3-c]pyrazol-3-yl)-3-oxo-N-phenyl-propanamide | 0.10 g |
| Lecithin | 0.07 g |
| Cocoa butter | 0.83 g |
| Total | 1.00 g |

| Formulation 4: Syrup | |
|---|---|
| 2-cyano-3-(1,4-dihydro-1-phenyl-[1]-benzothiopyrano[4,3-c]pyrazol-3-yl)-3-oxo-N-phenyl-propanamide, Sodium salt | 1.0 g |
| Gum tragacanth | 1.0 g |
| Methyl-p-hydroxybenzoate | 0.135 g |
| Propyl-p-hydroxybenzoate | 0.015 g |
| Polyoxymethylene sorbitan monolaurate | 5 g |
| Glycerine 30 Be | 5 g |
| Saccharose | 50 g |
| Natural Flavour | q.s. |
| Purified water to make | 100 g |

| Formulation 5: Cream | mg/g |
|---|---|
| 2-cyano-3-(1,4-dihydro-1-phenyl-[1]-benzothiopyrano[4,3-c]pyrazol-3-yl)-3-oxo-N-phenyl-propanamide | 20.0 |
| White petrolatum | 100.0 |
| Cetylstearyl alcohol | 72.0 |
| Mineral oil | 60.0 |
| Polypropylene glycol | 22.5 |
| 4-Chloro-m-cresol | 1.0 |
| Purified water to make | 1.0 g |

| Formulation 6: Ointment | mg/g |
|---|---|
| 2-cyano-3-(1,4-dihydro-1-phenyl-[1]-benzothiopyrano[4,3-c]pyrazol-3-yl)-3-oxo-N-phenyl-propanamide | 50.0 |
| Mineral oil | 50.0 |
| Propylene glycol | 50.0 |
| Petrolatum, to make | 1.0 g |

| Formulation 7: Suspension for intramuscular injection | |
|---|---|
| 2-cyano-3-(1,4-dihydro-1-phenyl-[1]-benzothiopyrano[4,3-c]pyrazol-3-yl)-3-oxo-N-phenyl-propanamide | 5.0 g |
| Aluminum monostearate | 2.0 g |
| Sesame oil to make | 100 ml. |

We claim:

1. A method for the treatment of a mammal suffering from suppression of myelopoiesis caused by cancer chemotherapy, cancer radiation therapy, immunosuppressant therapy following an organ or tissue transplantation, immunosuppressant therapy for an autoimmune disease, an autologous or allogenic bone marrow transplant, a burn, exposure to radiation or to a chemical which suppresses myelopoiesis, aplastic anemia, myelodysplastic syndrome or a congenital or acquired bone marrow disorder, the said method comprising administering thereto a therapeutically effective amount of a heteroaryl-3-oxopropanenitrile derivative of formula (I):

$$R_1-N^1-N^2\diagdown_{C(=O)CH_3-COCH\diagdown_Q^{CN}}$$

(structure with benzene ring bearing $R_2$, $R_3$ substituents, fused via X linker)

wherein
X represents $-CH_2-$, $-O-CH_2-$ or $-S-CH_2-$;
$R_1$ represents phenyl, the phenyl being unsubstituted or substituted by one or two halogen atoms;
$R_2$ represents:
  a) hydrogen, halogen or $C_1-C_6$ alkyl;
  b) $C_1-C_6$ alkoxy;
  c) nitro or amino;
  d) a $$-CH_2-N\diagup_{R''}^{R'}$$

group
  wherein R' and R'', taken together with the nitrogen atom to which they are linked, form a heterocyclic ring which is selected from the group consisting of N-pyrrolidinyl, N-piperazinyl, hexahydroazepin-1-yl, thiomorpholino, morpholino and piperidino which is unsubstituted or substituted by $C_1-C_6$ alkyl;

e) $C_2-C_7$ alkoxycarbonyl;
f) an $-NHCO(CH_2)_n$ COOR group, wherein n is zero and R is $C_1-C_6$ alkyl; or
g) a $C_2-C_7$ alkoxycarbonyl group substituted by a

group, wherein R' and R" are each a $C_1-C_6$ alkyl group; $R_3$ is as previously defined for $R_2$ above under a), b) and c); Q represents a

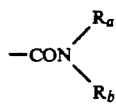

group
wherein $R_a$ represents hydrogen and $R_b$ represents a $-(A)_m-R_5$ group wherein m is zero or 1, A is $C_1-C_6$ alkylene and $R_5$ is phenyl, unsubstituted or substituted by one or two substituents independently selected form halogen, $CF_3$, and nitro; or a pharmaceutically acceptable salt thereof.

2. A method according to claim 1, wherein said derivative is selected from the group consisting of:
2-cyano-3-(1,4-dihydro-1-phenyl--benzothiopyrano pyrazol3-yl)-3-oxo-N-phenyl-propanamide;
N-benzyl-2-cyano-3-(1,4-dihydro-1-phenyl---benzothiopyranopyrazaol-3-yl)-3-oxo-propanamide;
2-cyano-N-(4-fluoro-phenyl)-3-(1,4-dihydro-1-phenyl-benzothiopyrano pyrazol-3-yl)-3-oxo-propanamide;
2-cyano-N-(4-fluoro-phenyl)-3-benzothiopyrano pyrazol-3-yl)-3-oxo-propanamide;
2-cyano-3-(1,4-dihydro-8-methyl-1-phenyl)-benzo thiopyrano pyrazol-3-yl)-3-oxo-N-phenyl-propanamide;
3-(8-chloro-1,4-dihydro-1-phenyl-benzothiopyrano pyrazol3-yl)-2-cyano-3-oxo-N-phenyl-propanamide;
N-(3-chloro-phenyl-2-cyano-3-(1,4-dihydro-1-phenyl---benzothiopyrano pyrazol-3-yl)-3-oxo-propanamide;
2-cyano-3-(1,4-dihydro-1-phenyl-indeno pyrazol-3-yl)-3-oxo-N-phenyl-propanamide;
2-cyano-N-(4-fluoro-phenyl)-3-pyrazol-3-yl)-3-oxo-propanamide;
2-cyano-N-(4-fluoro-phenyl)-3-pyrazol-3-yl)-3-oxo-propanamide;
N-(3-chloro-phenyl)-2-cyano-3-(1,4-dihydro-1-phenyl-indenopyrazol-3-yl)-3-oxo-propanamide;
2-cyano-3-(1,4-dihydro-1-phenyl-benzopyranopyrazol-3-yl)-3-oxo-N-phenyl-propanamide;
2-cyano-3-(1,4-dihydro-7-methyl-1-phenyl-indeno pyrazol-3-yl)-3-oxo-N-phenyl-propanamide;
3-(7-tert.butyl-1,4-dihydro-1-phenyl-indeno pyrazol-3-yl)-2-cyano-3-oxo-N-phenyl-propanamide;
2-cyano-3-(7-fluoro-1,4-dihydro-1-phenyl-indeno pyrazol-3-yl)-3-oxo-N-phenyl-propanamide;
2-cyano-N-(4-fluoro-phenyl)-3-(7-fluoro-1,4-dihydro-1-phenylindeno pyrazol-3-yl)-3-propanamide;
3-(7-tertbutyl-1,4-dihydro-1-phenyl-indeno pyrazol-3-yl)-2-cyano-N-(4-fluoro-phenyl)3-oxo-propanamide;
2-cyano-N-(4-fluoro-phenyl)-3-(1,4-dihydro-7-methyl-1-phenylindeno pyrazol-3-yl)-3-oxo-propanamide;
3-(6-tert butoxycarbonyl-1,4-dihydro-1-phenyl-benzothiopyrano pyrazol-3-yl)-2-cyano-3-oxo-N-phenyl-propanamide;
3-(5-tert butoxycarbonyl-1,4-dihydro-1-phenyl-indeno pyrazol3-yl)-2-cyano-3-oxo-N-phenyl-propanamide;
2-cyano-3-(1,4-dihydro-5-morpholinomethyl-1-phenyl-indeno pyrazol-3-yl)-3-oxo-N-phenyl-propanamide;
2-cyano-3-(8-fluoro-1,4-dihydro-6-morpholinomethyl-1-phenyl-benzopyrano pyrazol-3-yl)-oxo-N-phenyl-propanamide; and pharmaceutically acceptable salts thereof.

3. A method for the treatment of a mammal suffering from a disease having an auto-immune basis, which method comprises the separate, simultaneous or sequential administration thereto of:
a therapeutically effective amount of a compound of formula (I) as defined in claim 1, or a pharmaceutically acceptable salt thereof, and
a therapeutically effective amount of an immunosuppressant agent which causes suppression of myelopoiesis.

4. A method according to claim 3 wherein the immunosuppressant agent is selected from the group consisting of cyclophosphamide, azathioprine, 6-mercaptopurine, methotrexate and corticosteroids.

* * * * *

UNITED STATES PATENT AND TRADEMARK OFFICE
CERTIFICATE OF CORRECTION

PATENT NO. : 5,206,258
DATED : April 27, 1993
INVENTOR(S) : Gianfederico DORIA et al It is certified that error appears in the above-identified patent and that said Letters Patent is hereby corrected as shown below:

On the title page, in Item [54], after "CLINICAL" insert -- CONDITIONS --.

Column 1, line 4, after "CLINICAL" insert -- CONDITIONS --.

Signed and Sealed this

Thirtieth Day of November, 1993

Attest:

BRUCE LEHMAN

Attesting Officer

Commissioner of Patents and Trademarks